United States Patent [19]

Johnson et al.

[11] 4,396,784

[45] Aug. 2, 1983

[54] HYDROGENATION OF FLUOROACIDS WITH RHENIUM-FLUORIDED ALUMINA CATALYST

[75] Inventors: Marvin M. Johnson; Gerhard P. Nowack; Paul S. Hudson, all of Bartlesville, Okla.; Benedict H. Ashe, Jr., deceased, late of Bartlesville, Okla., by Patricia O. Ashe, executrix

[73] Assignee: Phillips Petroleum Company, Bartlesville, Okla.

[21] Appl. No.: 354,857

[22] Filed: Mar. 4, 1982

Related U.S. Application Data

[60] Continuation of Ser. No. 162,541, Jun. 24, 1980, abandoned, which is a division of Ser. No. 64,283, Aug. 6, 1979, abandoned.

[51] Int. Cl.$^3$ ............................................. C07C 29/136
[52] U.S. Cl. .................................................... 568/842
[58] Field of Search ......................................... 568/842

[56] References Cited

U.S. PATENT DOCUMENTS 3,726,810  4/1973  Myers.
4,205,017  5/1980  Bjorason.

OTHER PUBLICATIONS

Broadbent et al., J Org. Chem., 24 (1959) pp. 1827–1854.

*Primary Examiner*—Howard T. Mars

[57] ABSTRACT

A fluoroacid is continuously hydrogenated to a corresponding alcohol by contact with a catalyst comprising at least one of rhenium and a hydrogen reducible rhenium compound supported on a fluorided alumina catalyst support. In one embodiment perfluorobutyric acid is catalytically reduced to 2,2,3,3,4,4,4-heptafluoro n-butanol employing a fluorided activated alumina impregnated with perrhenic acid.

8 Claims, No Drawings

HYDROGENATION OF FLUOROACIDS WITH RHENIUM-FLUORIDED ALUMINA CATALYST

This is a continuation of application Ser. No. 162,541, filed June 24, 1980, abandoned, which is a division of application Ser. No. 64,283, filed Aug. 6, 1979, now abandoned.

BRIEF SUMMARY OF THE INVENTION

A fluoroacid is hydrogenated to corresponding alcohol employing a catalyst or contact mass comprising rhenium or a hydrogen reducible rhenium compound supported on a fluorided alumina catalyst support or on an aluminum fluoride catalyst support.

DETAILED DESCRIPTION

This invention relates to the hydrogenation of fluoroacids. In one of its aspects, it relates to the hydrogenation of a fluoroacid to a corresponding alcohol. In another of its aspects, the invention relates to the use of a rhenium hydrogenation catalyst. In a more specific aspect of the invention, it relates to use of such a catalyst supported upon a catalyst support which can be at least one of a fluorided alumina and an aluminum fluoride.

In one of its concepts, the invention provides a process for the continuous hydrogenation of a fluoroacid to a corresponding alcohol which comprises subjecting said acid to contact with a catalyst comprising at least one of rhenium and a hydrogen reducible rhenium compound supported on a fluorided alumina catalyst support. Herein and in the claims terms "fluorided alumina" and "aluminum fluoride" are to be considered to be functionally equivalent.

In another of its concepts, the invention, in a preferred form, produces the fluorided alumina catalyst support by treating at increasing temperatures a catalytic grade of alumina, e.g., gamma or eta activated alumina that has been formed into tablets or granules, with gaseous hydrogen fluoride, preferably diluted with an unreactive gas such as nitrogen.

In a more specific concept, the invention provides a process for hydrogenating a fluoroacid having the general formula RCOOH to a corresponding fluoroalcohol having the general formula RCH$_2$OH, wherein R is an aliphatic hydrocarbon radical in which at least one hydrogen atom has been replaced by a fluorine atom. In still another concept, R is a saturated radical.

The hydrogenation of trifluoroacetic acid and heptafluorobutyric acid with rhenium heptoxide reduced in situ as catalyst is reported in the *Journal of Organic Chemistry*, December, 1959, pages 1827–1854.

In the article, autoclaves or rocking bombs were employed in runs which were conducted as batch operations.

It is desirable to have an effective carrier or catalyst support permitting continuous hydrogenation. It is important that the support be effective to give acceptable conversions and yields. Also, the catalyst should be one which will maintain its activity over an acceptable, extended period of time.

It is an object of this invention to hydrogenate a fluoroacid. It is another object of this invention to provide a continuous process for the hydrogenation of a fluoroacid. It is a further object of this invention to convert a fluoroacid to a corresponding alcohol. A still further object of the invention is to provide a process employing an effective support for a rhenium catalyst. Further, an object of the invention is to provide a process for the continuous hydrogenation of a fluoroacid employing a rhenium catalyst.

Other aspects, concepts, objects, and the several advantages of the invention are apparent from a study of this disclosure and the appended claims.

According to the present invention, there is provided a process for the continuous hydrogenation of a fluoroacid to a corresponding alcohol which comprises subjecting said acid to contact with a catalyst comprising at least one of rhenium and a hydrogen reducible rhenium compound supported on a fluorided alumina catalyst support.

A catalyst, as described, is prepared by treating at increasing temperatures a catalytic grade of alumina, for example, gamma or eta activated alumina, preferably formed into tablets or granules, with gaseous hydrogen fluoride, preferably diluted with inert gas such as nitrogen, the fluorided alumina containing at least about 50 wt % fluorine. Rhenium is added to the support by impregnation in a now preferred embodiment of the invention.

The rhenium can be added to the support in any suitable manner. For example, the rhenium can be added as an aqueous solution of ammonium perrhenate or perrhenic acid. The mass obtained is dried to remove solvent. The catalyst is then prepared for reaction by reducing it in a stream of flowing hydrogen at about 1000–5000 GHSV while raising the temperature of it to about 315° C. Ordinarily, the finished catalyst will contain about 0.1 to about 20 wt. % rhenium, calculated as the element. It is now preferred that the catalyst contained about 0.5 to about 10 wt. % rhenium.

At reaction conditions defined below the catalyst of this invention is active and selective to hydrogenate fluoroacids having the general formula RCOOH to fluoroalcohol having the general formula RCH$_2$OH, where R is an aliphatic hydrocarbon radical in which from one to all hydrogen atoms have been replaced by fluorine atoms. It is preferable that R be a saturated radical. Unsaturated acids would be hydrogenated at reaction conditions but may undergo possibly undesirable rearrangement of fluorine atoms of dehydrofluorination resulting in a less pure reaction product. R will contain at least one carbon atom and is limited in size to compounds having physical properties that are compatible with reaction conditions, e.g., that are fluids or amenable to being rendered fluid under reaction conditions.

Examples of fluoroacids now preferred, and which are readily amenable to hydrogenation in the process of this are mono-, di- and trifluoracetic acid, perfluoropropionic acid. perfluorobutyric acid, perfluorocaproic acid, perfluorocapric acid, the partially fluorinated derivatives of these acids, and the like.

The reaction of the invention can be illustrated by the equation

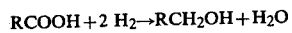

wherein R is a saturated aliphatic radical that contains fluorine. Under the conditions of reaction, fluorine, generally in low quantities, is removed from the organic acid, probably as hydrogen fluoride. This has an adverse effect on conventional catalyst supports.

Hydrogenation of fluoroacids to the corresponding fluoroalcohols is effected by continuously passing the acid admixed with hydrogen gas over a fixed bed of the catalyst at an elevated temperature and pressure. Reactant liquid is preferably passed down-flow rather than up-flow through the catalyst bed to prevent accumulation of any liquid product present at reaction conditions.

The rate of hydrogenation is favored by elevated pressure, and pressures between about 50–1000 pounds per square inch gauge ($4.5 \times 10^5$–$7.0 \times 10^6$ Pa) can be used.

The temperature at which hydrogenation is effected requires good control to attain optimum selectivity. If it is too low conversion of the acid is incomplete, or can stop at the corresponding fluoroaldehyde instead of proceeding to the alcohol. If it is too high the reactants and products are susceptible to hydrogenolysis of carbon-carbon bonds and also to dehydrofluorination. Temperatures of from about 175° to about 275° C. can be used. The now preferred temperature range for hydrogenation is in the range of from about 205° to about 235° C.

Hydrogenation of the carboxylic acid to the corresponding alcohol requires two moles of hydrogen per mole of acid. However, to prevent accumulations of carbonaceous residues on the catalyst the preferred ratio is about 3–5 moles per mole of acid; higher ratios of hydrogen can be used although it may be uneconomic to do so. In Example 2 the hydrogen to acid mole ratio being fed is 10–12:1.

The rate at which the fluoroacid is fed to the hydrogenation reactor, expressed as volumes of liquid per volume of catalyst per hour (LHSV), can range from about 0.1 to about 10:1, preferably the rate will be from about 0.5 to about 2 LHSV.

Alcohol that is formed by hydrogenating fluoroacids can be recovered by cooling vapor effluent from the reaction zone to condense a liquid product. This can be subjected to purification steps as required to separate the alcohol from any unreacted acid or by products that have been produced.

Fluoroalcohols prepared by this process have been used to produce polymers that have unusual properties. Thus, reaction with poly(dichlorophosphazene) has produced an elastomer designated PNF-200 by The Firestone Tire and Rubber Company that has superior high and low temperatures properties and excellent grease (hydrocarbon liquid) resistance.

Runs to illustrate this invention were made using a pipe reactor that was 30" long and consisted of a ¼" aluminum pipe that had been reduced in diameter by machining, then pressed inside a ½" o.d. ×0.035" wall thickness 316 stainless steel tube. The reactor was mounted vertically in a 25" long, three-zone electrically heated tube furnace. A ⅛" o.d. stainless steel thermocouple well was centered in the reaction. Hydrogen was metered into the reactor through a calibrated rotameter. Liquid fluoroacids were pumped from a calibrated buret with a positive displacement pump. Reaction products passed through a trap cooled to 0° C., then through a trap cooled in dry ice, and uncondensibles were vented. Samples were taken from these traps and analyzed by gas liquid chromatography using Carbonwax 20M supported on Teflon Tee-6 support, in a glass column.

EXAMPLE 1

Catalyst preparation. Harshaw Al-X-256A-1-1-activated alumina that has been dried in air at 480° C. was fluorided by treatment with a 10:1 nitrogen:hydrogen fluoride gas mixture, starting at about 150° C., then increasing the temperature to about 315° C. Finally it was heated in nitrogen only to 427° C. Analysis showed it to contain 58.2 wt. % fluorine, and it had 28 m²/g surface area. This fluorided alumina (37.6 g) was impregnated with 14 ml of aqueous solution that contained 1.30 g rehenium as perrhenic acid. After drying, the material was heated in flowing hydrogen to 315° C. and held there overnite. This composition that contained 3.3 wt. % rehnium was designated catalyst A.

Catalyst B was prepared in a similar manner and also contained 3.3 wt % Re. It was supported, however, on alumina similar to that used above but not fluorided.

EXAMPLE 2

Catalyst A was used in a run to reduce catalytically perfluorobutyric acid to 2,2,3,3,4,4,4-heptafluoro n-butanol. Nine ml (10.7 g) of the catalyst were placed in the reactor, occupying 8" of length. The volume above and below the catalyst was filled with alpha-alumina, and the catalyst was centered inside the funace. The hydrogen:acid mole ratio being fed was 10–12:1, with acid being pumped at 0.75 LHSV. Reaction pressure was 300 psig throughout the run but the temperature varied as shown below in Table I. The second column there shows the cumulative weight of acid that the 10.7 g catalyst was exposed to. Condensed liquid product from the run appeared as two immiscible phases—an essentially pure water layer floating on the denser organic layer. Analyses in Table I are of the organic phase.

TABLE I

| Sample | Total Acid, g | T, °C. | GLC Analyses, Wt. % | | | |
|---|---|---|---|---|---|---|
| | | | H$_2$O | Alcohol | Acid | Aldehyde |
| I | 43.2 | 229–238 | 12 | 88 | 0 | 0 |
| II | 76.2 | 206–212 | 10 | 90 | 0 | 0 |
| III | 101.1 | 172–180 | 18 | 60 | 18.4 | 3.6 |
| IV | 165.5 | 211 | 12 | 87.9 | 0.14 | 0 |
| V | 319.5 | 212 | 14.5 | 85.5 | 0.04 | 0 |
| VI | 511.2 | 213 | 13 | 86.7 | 0.15 | 0 |
| Catalyst treated for 60 hours with flowing H$_2$ at 204° C., 1 atm. | | | | | | |
| VII | 621.9 | 211 | 11.4 | 88.6 | 0 | 0 |
| VIII | 957.8 | 211 | 14.2 | 85.4 | 0.2 | 0.2 |
| IX | 1197.2 | 211 | 14.7 | 83.7 | 1.2 | 0.4 |
| X | 1598.2 | 205 | 14.2 | 54.6 | 30.1 | 1.1 |

Although water comprises a significant fraction of the phase its concentration is not pertinent to estimating conversion or selectivity. Except for samples III and X acid conversion was high as was selectivity to the corresponding alcohol. The temperature for sample III was too low to effect complete conversion, and at sample X, when about 150 weights of acid per unit weight of catalyst had been processed the temperature was apparently too low.

EXAMPLE 3

Catalyst B was used to make a run essentially identical to the one described in the preceding example. The same fluoroacid and hydrogen, in the same ratio and at the same space rate, were reacted at the same pressure, but again at varying temperatures. In this run 10.5 ml (7.8 g) of catalyst were used. Reaction products were collected in four portions during the run. Table II summarizes catalyst temperature and the composition of the organic phase collected during each period.

TABLE II

| Sample | Total Acid, g | T, °C. | GLC Analyses, Wt. % | | | |
|---|---|---|---|---|---|---|
| | | | H$_2$O | Alcohol | Acid | Aldehyde |
| XX | 29.1 | 176–185 | 17.7 | 49.9 | 21.3 | 11.1 |
| XII | 54.1 | 176 | 10.1 | 26.2 | 54.5 | 9.2 |
| XIII | 66.5 | 208–212 | 16.0 | 67.5 | 16.0 | 0.5 |
| XIV | 101.9 | 210 | 13.2 | 47.9 | 37.8 | 1.1 |

This run started at low temperature and samples XI and XII reflect that condition with a high concentration of unconverted acid and partially converted acid—the corresponding aldehyde. Sample XIII, collected at a temperature at which rhenium supported on fluorided alumina was active, showed greater conversion than was observed at the lower temperature but it failed to sustain the activity. Sample XIV at about the same temperature showed much lower conversion. A rapid decline in activity with time characterizes the behavior of the catalyst prepared by impregnating unfluorided activated alumina with rhenium.

The polymers which can be prepared with the alcohols of the invention exhibit good properties at high and at low temperatures. They are resistant to degradation, to hydrocarbon liquids and possess useful water repellency.

EXAMPLE 4

Rhenium supported on a fluorided alumina as herein described was used to hydrogenate trifluoroacetic acid, $CF_3CO_2H$ to trifluoroethanol $CF_3CH_2OH$ at about 300 psig, 280° C. and at 0.3 LHSV of the acid. The yield was about 100 percent.

The catalyst was made by impregnation of fluorided alumina with perrhenic acid solution, followed by reduction in hydrogen at about 310° C. Reasonable variation and modification are possible within the scope of the foregoing disclosure and the appended claims to the invention, the essence of which is that a continuous process for the hydrogenation of a fluoroacid, as described, employing a rhenium hydrogenation catalyst supported on a fluorided alumina, also as described, to produce a corresponding fluoro-alcohol and a catalyst comprising essentially rhenium or a hydrogen reducible rhenium compound on a fluorided alumina catalyst support have been set forth.

It is claimed:

1. A process for the continuous hydrogenation of an organic fluoroacid to a corresponding alcohol which comprises subjecting said acid to contact with a catalyst under hydrogenation conditions consisting essentially of at least one of rhenium and a hydrogen reducible rhenium compound supported on a fluorided alumina catalyst; wherein said organic fluoroacid is represented by the general formula RCOOH wherein R is an aliphatic hydrocarbon radical in which at least one hydrogen atom has been replaced by a fluorine atom; and wherein said hydrogenation is conducted at a temperataure in the approximate range of from about 175° to about 275° C.

2. A process according to claim 1 wherein R is a saturated radical.

3. A process according to claim 2 wherein the fluoroacid is at least one selected from mono-, di-, and tri- fluoroacetic acids, perfluoropropionic acid, perfluorobutyric acid, perfluorocaproic acid, perfluorocapric acid, and partially fluorinated derivatives thereof.

4. A process according to claim 1 wherein the fluoroacid is continuously passed admixed with hydrogen gas over a fixed bed of the catalyst at an elevated temperature and pressure.

5. A process according to claim 4 wherein a downward flow of reactants is employed.

6. A process according to claim 4 wherein the temperature is in the range of from about 205° to about 235° C.

7. A process according to claim 1 wherein the fluoroacid is perfluoroacetic acid.

8. A process according to claim 1 wherein the acid is perfluorobutyric acid.

* * * * *